: US006033887A

United States Patent [19]
Charpentier

[11] Patent Number: 6,033,887
[45] Date of Patent: Mar. 7, 2000

[54] DEHYDRATED POLYSACCHARIDE GEL CONTAINING MICROORGANISMS, A SUGAR AND A POLYOL FOR PRODUCING FERMENTED DRINKS

[75] Inventor: Monique Charpentier, Epernay, France

[73] Assignee: Champagne Moet & Chandon, Epernay, France

[21] Appl. No.: 08/851,313

[22] Filed: May 5, 1997

[51] Int. Cl.$^7$ ............... C12N 11/10; C12N 1/04; C12G 1/00; C12C 11/00

[52] U.S. Cl. ............... 435/178; 426/11; 426/13; 426/15; 435/182; 435/260

[58] Field of Search .................. 435/178, 182, 435/260; 426/11, 13, 15

[56] References Cited

U.S. PATENT DOCUMENTS

| | | | |
|---|---|---|---|
| 1,420,557 | 6/1922 | Klein | 435/255.7 |
| 3,015,128 | 1/1962 | Somerville, Jr. | 425/5 |
| 3,310,612 | 3/1967 | Somerville, Jr. | 264/4 |
| 3,396,116 | 8/1968 | Adams et al. | 428/402.2 |
| 3,407,072 | 10/1968 | Aizawa et al. | 426/62 |
| 4,246,349 | 1/1981 | Messing et al. | 435/176 |
| 4,386,895 | 6/1983 | Sodickson | 425/5 |
| 4,663,286 | 5/1987 | Tsang et al. | 435/178 |
| 4,764,472 | 8/1988 | Pomper et al. | 435/256 |
| 5,389,532 | 2/1995 | Divies et al. | 435/178 |
| 5,627,062 | 5/1997 | Divies et al. | 435/178 |

FOREIGN PATENT DOCUMENTS

| | | |
|---|---|---|
| 0 065 376 | 11/1982 | European Pat. Off. . |
| 0140336 | 10/1984 | European Pat. Off. . |
| 2 320 349 | 3/1977 | France . |
| 2 359 202 | 2/1978 | France . |
| 2 432 045 | 2/1980 | France . |
| 2 519 022 | 7/1983 | France . |
| 2 601 687 | 2/1988 | France . |
| 0 173 915 | 3/1986 | Germany . |
| 57-150385 | 3/1981 | Japan . |
| 60-99336 | 6/1995 | Japan . |
| 1158662 | 7/1969 | United Kingdom . |

OTHER PUBLICATIONS

*Microcapsule Processing and Technology*, "In–Liquid Curing Coating Process (Orifice Process)," Asaji Kondo, 1979, pp. 62–66.

*Biotechnology and Bioengineering*, vol. XXII, (1980) "Gas Production by Immobilized Microorganisms: Theoretical Approach," P. G. Krouwel, et al., pp. 681–687.

*Journal AWWA*, (1979) 71 (6), "Polyelectrolyte Selection for Direct Filtration," Vernon L. Stump, et al., pp. 338–342.

C. Divies, "Application du Marquage Par La $^3H_6$–Thymidine A L'Etude de la Multiplication de *Lactobacillus Casei* Inclus Dans un Gel de Polyacrylamide," *Annales de Microbiologie*, 1977, pp. 349–358.

Becker et al., "Conservation of Yeasts by Dehydration," *Biotechnology*, vol. 15, pp. 162–171, 1987.

Y. Bashan, "Alginate Beads as Synthetic Inoculant Carriers for Slow Release of Bacteria That Affect Plant Growth," *Applied and Environmental Microbiology*, May 1986, pp. 1089–1098.

*Primary Examiner*—David M. Naff
*Attorney, Agent, or Firm*—Smith, Gambrell & Russell, LLP

[57] ABSTRACT

Improved fermentation activity of microorganisms in a polysaccharide gel such as an alginate gel is obtained after dehydration, staorage and rehydration by soaking the gel containing the microorganisms prior to dehydration in a sugar solution to provide in the gel an amount of sugar of at least 100 g/kg and less than 500 g/kg of gel, preferably less than 300 g/k of gel. The dehydration may be carried out in a fluidized bed or by lyophilization. The gel may be in the form of beads or fibers having a double layer structure formed by an internal layer or core of gel containing the microorganisms and an external lay er or envelope of gel essentially devoid of the microoraganisms. The sugar is preferably xylose, glucose, fructose, lactose or sucrose, and the sugar solution may contain a polyol such as sorbitol, inositol or glycerol to provide in the gel an amount of polyol of at least 30 g/kg of gel. The sugar solution may also contain a non-ionic surfactant such as sorbitan monostearate as a protecting substance to fur ther improve fermentation activity. The microorganisms in the gel are preferably yeast, and after rehydration the yeast containing gel is used in producing a fermented drink such as in secondary fermentaion of wine to produce sparkling wine or champagne.

88 Claims, No Drawings

DEHYDRATED POLYSACCHARIDE GEL CONTAINING MICROORGANISMS, A SUGAR AND A POLYOL FOR PRODUCING FERMENTED DRINKS

BACKGROUND OF THE INVENTION

1. Field of the Invention

The present invention relates essentially to a process of producing a dehydrated polysaccharide gel containing microorganisms for preparing fermented drinks, the dehydrated gels obtained therefrom, and their use for the preparation of fermented drinks, notably for the second fermentation of wine to produce sparkling wine and notably champagne.

2. Description of the Related Art

In the state of the prior art, it is known that immobilized microorganisms can be used in the production of fermented drinks such as wine and beer (FR-A-2 320 349 and FR-A-2 359 202). Their use has also been suggested for classical champagnization (FR-A-2 432 045) as well as for the manufacture of sparkling drinks with a variable degree of alcohol (FR-A-2 601 687). These publications, as well as others (in particular JP-A-57-150 385 and EP-A-173 915) have emphasized the performances of reactors with immobilized cells.

These techniques have made it possible to carry out fermentations with mixtures of microorganisms of different categories (mixture of lactic acid bacteria and mixture of yeast).

However, the implementation of the process on an industrial scale came up against the difficulty of having particles available which are capable of being preserved for a long period.

Microorganisms in the immobilized form, for instance in a gel, may be used without an appreciable drop of activity over long periods when the nutrition of the microorganisms concerned is respected.

It has been possible to note a toxicity of the products of fermentation which leads to a partial ageing of the cells (article by DIVIES et al. in Annales de microbiologie, 1977, pages 349–358).

It was thus preferred in this particular case to use a battery of reactors of defined life time and to carry out the partial renewal of the microbial particles in a programmed manner.

Problems of mechanical resistance of the gel entrapping microorganisms have also arisen and are described in JP-A-57-150 385.

It thus appears crucial industrially to plan the elaboration of the particles for inclusion of the microorganisms and to centralize the production of them. It is also necessary to bring about the inclusion of the microorganisms in the gels which ensures an excellent viability of them over a period of time.

However, it because apparent that the microorganisms entrapped in the gels were rather sensitive and could not survive after a storage over a long period of time.

In order to overcome this drawback, it has already been suggested to store the gel in a dry form.

The commercial preparations of microorganisms entrapped with a dried gel naturally need to be capable of rehydration and to maintain excellent viability after rehydration, and stability of the structure of the gel as well as its mechanical properties.

Certain solutions have been proposed which permit storage at a relatively low temperature range of about 4 to 10° C. in a protective packaging over periods of time which may reach 6 months to 1 year (see BEKER and RAPOPORT in Advances in Biochemical Engineering and Biotechnology, Volume 35, 1987, pages 128 to 171). In the paragraph heading "Applications of dehydration for production of active dry yeasts", beginning on page 162, and in particular the passage on page 163, lines 13 to 15, BEKER and RAPOPORT report that the usual amount of hydrophilic wetting agents used as protective drying agents is from 0.5 to 5% of the dry weight of the yeasts to be dried.

In addition, U.S. Pat. No. 3,407,072 states in column 2, lines 43 to 46, in relation to protective drying agents described in column 2, lines 8 to 11, concentrations ranging from about 2 to 40 g/kg of compressed yeasts to be dried. From the examples, it appears that this concentration is essentially the same when expressed per liter of yeasts in suspension. Therefore, this disclosure is consistent with the usual concentration of the protective drying agent set forth by BEKER and RAPOPORT hereinabove which ranges from 5 to 50 g/kg of material to be dried.

The TATE document EP-A-0 065 376 describes a process for the preparation of enzymes immobilized in a gel which is then dried if need be and, after drying, is put in contact with glycerol (page 10, 2nd paragraph and Claim 3). A placing in contact after drying does not make it possible to preserve the structure of the gel and renders its rehydration difficult. This problem is solved by the present invention and which will be described below.

The document FR-A-2 519 022 describes a process for the preparation of inocula with long viability and which have an improved resistance to temperature which comprises a drying of the microorganisms in accordance with various drying processes. In its introduction, this documents describes many prior art documents which relate to drying gels enclosing microorganisms.

According to this FR-A-2 519 022 document, at the beginning of the process, a culture of microorganisms is grown in a standard culture medium for several days.

A gelable polymer, notably a polysaccharide, such as xanthane or alginate, may be added to this culture medium.

After gelation, which enables the inclusion of a microorganism in the culture medium, drying is undertaken in order to reach a water activity value in the inoculum lower than 0.5, this value being maintained during storage, see claim 1 in particular. Preferably, the water activity in the inoculum is maintained below 0.3 and preferably even below 0.1, see claim 2.

It is to be noted that, according to this document, no consideration is taken regarding the special problem of the rehydration of the gel so as to obtain a rehydrated gel having a structure approximately identical to that it had before its dehydration.

Now, experiments have shown that the dehydrated or dried particles obtained by the method described in this document, could not be properly rehydrated. At best, in the presence of culture medium, the rehydration remains limited at 20% humidity, the particles always remaining very small, dried up, very hard and un-graded with respect to size.

If a supplementation with hydrophilic substances such as carrageenan or carob seed grain is carried out, this causes the gel to become brittle without improving the rehydration of the gelled polymer, and this is particularly true in the case of the use of an alginate. At best, too low viabilities incompatible with an industrial use may be obtained.

Hence, it appears necessary to dispose of easily re-hydratable gels which contain a maximum of viable microorganisms after rehydration, and which do so even after a long period of storage.

U.S. Pat. No. 5,389,532 discloses a first improvement enabling obtaining dried or essentially dehydrated gels, which are easily re-hydratable, contain a satisfactory viable microorganisms content after rehydration and which can be stored during a long period of time.

In this patent, it is disclosed a pre-treatment of the gels entrapping the microorganisms in a solution containing at least 500 g/l of hydrophilic substances, wherein the best compound is sucrose, which is preferably used at about 1,000 g/l, prior performing a drying of the gels.

Now, it has been discovered that a pre-treatment with such a high concentration of hydrophilic substances, in particular sucrose or sorbitol, provides a drawback of rendering the drying more difficult with a corresponding risk of damaging the microorganism cells entrapped in the gel and or requiring the preparation of such highly concentrated solutions, which are also relatively costly on an industrial scale.

SUMMARY OF THE INVENTION

The aim of the present invention is therefore to solve the new technical problem consisting in providing a solution which enables doing away with dried or essentially dehydrated gels which are easy to re-hydrate, and which contain a high ratio of viable microorganisms after rehydration, and even after a prolonged period of storage, by using compounds capable of protecting the gels during the drying step, which are used at a rather low concentration range.

Another aim of the present invention is to solve the new technical problem consisting in providing a solution which enables disposing gels which contain a high ratio of viable microorganisms after rehydration, which preserve an essentially unchanged structure of the gel after rehydration, which maintain a good stability of this gel compatible with an industrial use of the re-hydrated gel, by using compounds protecting the gels during the drying step, which are used at a relatively low concentration range.

These technical problems are solved simultaneously for the first time by the present invention in an extremely simple manner which can be used on an industrial scale.

It has indeed been discovered, surprisingly and unexpectedly, that sugar, which is a hydrophilic substance of low molecular weight of the type disclosed in U.S. Pat. No. 5,389,532 could still have at least the same efficiency or even greater efficiency if it is used at a lower concentration, namely below 500 g/l.

According to a first aspect, the invention relates to a process for the preparation of a gel in at least partially dehydrated entrapping microorganisms, said microorganisms exhibiting an improved fermentation activity after rehydration, comprising:

(a) dispersing the microorganisms in a gellable polysaccharide solution;

(b) gelling the polysaccharide solution containing the microorganisms to form a gel entrapping the microorganisms;

(c) soaking the gel entrapping the microorganisms in a solution containing a sugar in a predetermined concentration and for a period of time sufficient to reach equilibrium, said predetermined sugar concentration being sufficient to obtain said gel containing said sugar in an amount ranging between at least 100 g/kg and less than 500 g/kg of gel;

(d) separating the soaked gel from the said solution of sugar and recovering the gel; and (e) drying the gel to obtain an at least partially dehydrated gel.

According to an advantageous embodiment, the concentration in sugar ranges between at least 100 g/kg and less than 300 g/kg of the gel prior to dehydration. By using such a concentration of sugar inside said range, the drying step of said process does not require drying conditions which may have significant detrimental effects upon the microorganism cells, notably due to a long drying time.

According to another advantageous embodiment, the sugar content is at least 200 g/kg of the gel prior to dehydration.

It must be noted that in the present invention, a very convenient industrial sugar content is used, which is clearly less costly than the high amounts of at least 500 g/l and in practice of 1,000 g/l of sugar recommended in U.S. Pat. No. 5,389,532. Moreover, a high sugar content like in this U.S. patent renders more difficult the drying of the gel.

According to a particularly advantageous embodiment of the process according to the invention, the sugar is selected from the group consisting of aldoses, ketoses and diholosides. More precisely, the aldose may be xylose or glucose, the ketose may be fructose, and the diholoside may be lactose or sucrose. This sugar may be used alone or in association or combination with a low molecular weight polyol, such as sorbitol, inositol or glycerol. In a preferred embodiment of the process according to the invention, the sugar is used in the soaking solution in combination with a low molecular weight polyol also present in the soaking solution. Further, when the sugar is combined with a low molecular weight polyol, the polyol is used in the soaking solution in a content ranging from at least 30 g/l to less than 500 g/l, and more preferably at least 30 g/l to less than 300 g/l, and even more preferably a content in polyol of at least 50 g/l to less than about 200 g/l. Sucrose constitutes the sugar particularly preferred in the process. Among the low molecular weight polyols, glycerol is preferred.

According to the invention, the soaking pre-treatment of the gels entrapping the microorganisms in the solution containing at least a sugar along or said sugar in combination with a low molecular weight polyol such as sorbitol, inositol and glycerol, and preferably glycerol, enables performing an osmotic dehydration by transferring a significant amount of water from the gels towards the solution and solute goes from the solution, namely the sugar alone or the sugar with the polyol, towards the gels. This osmotic dehydration made under the conditions of the process of the invention enables lowering the water activity (also referred to as the abbreviation Aw) to a value for which there is no longer any microorganism activity. It is usually accepted by those skilled in the art that it is necessary to obtain a water activity Aw of less than 0.5 to obtain such a result of lack of activity of cells, see FR-A-2,519,022 and also EP-A-0,065,376.

The osmotic dehydration is also necessary to prepare gels containing microorganisms for a drying step to obtain at least partially dehydrated gels. In the case of a lack of such an osmotic dehydration with a sugar alone or a sugar in combination with a polyol, the gel shrinks so heavily during the drying that it hardens irreversibly and is no longer above to be re-hydrated. The osmotic dehydration of the invention allows preserving the physical integrity of the gel, while also preserving the viability and fermentation activity of the microorganisms at a satisfactory level, as it will be shown further on and notably with the tests made.

According to another advantageous embodiment of the invention, the gel further contains an additional protecting substance in a sufficient concentration to improve the viability of the microorganisms during the drying step of the invention process and the possible storage, and to improve the fermentation activity of said microorganisms after the rehydration step. Preferably, such an additional protecting substance is a non ionic surfactant, notably a sorbitan ester with a fatty acid, more preferably selected from the group consisting of sorbitan monolaurate, sorbitan monopalmitate, sorbitan monostearate and sorbitan monooleate.

According to the best mode, said sorbitan ester is sorbitan monostearate, commercially available as Span 60® or Arlacel 60®.

Advantageously, said additional protecting substance is added at the first step of the process according to the invention, in the gelable solution.

According to another embodiment of the invention, the said additional protecting substance may be added in the soaking solution instead of being added in said gelable solution.

When sorbitan monostearate is used to protect yeast, its concentration is of about 1 g for 100 g of dry yeast commercially available used for preparing the dispersion in the gelable solution.

According to another advantageous characteristic of the process according to the invention, a culture of cells of microorganisms is grown until the stationary phase is reached, which corresponds in particular in the case of yeasts to a low degree of budding or the initiation of division. Preferably, this low degree of budding is lower than 5%. This makes it possible to unexpectedly increase the viability of the microorganisms, particularly in the case of the yeasts.

In accordance with another advantageous characteristic of the process according to the invention, a gel is prepared which has a double layer structure comprising an internal layer or core of gel containing the cells of the microorganisms and an external layer or envelope of gel which is practically devoid of microorganisms. This gel may be in the form either of beads, or fibers, as is well known in gelation techniques.

In order to produce a gel which has a double layer structure, the previously known processes may be used, such as those described for example in the document JP-A-57-150 385, by preferably using the process described in this document which consists in forming the external layer or envelope with a gellable solution. It is also possible to use the technique described in the document GB-A-1 158 662 or U.S. Pat. No. 4,386,895 or U.S. Pat. No. 3,396,116, or even EP-A-0 140 336 or U.S. Pat. No. 3,015,128 or U.S. Pat. No. 3,310,612 or even the techniques of inclusion preparations described in an article by P. B. Krouvel in Biotechnology and Bioengineering (1980), volume 22, page 681 or the document Microcapsules Processing and Technology (Asaju Kondo) 1979, pages 62 to 66.

In accordance with a particularly advantageous characteristic of the process according to the invention, the thickness of the external layer or envelope, in the case of beads having a diameter of about 2 to 4 mm, is less than 0.8 mm.

In accordance with another advantageous characteristic of the process according to the invention, a drying of the gel is carried out until an activity of water lower than about 0.5 is obtained.

In accordance with another advantageous characteristic of the process according to the invention, the above-mentioned drying is carried out in an air stream, the air temperature and the time of drying being controlled so as to prevent the substantial mortality of the microorganisms. The parameters of temperature and time are well-known to those skilled of the art. Typically, temperature and drying time may be, in particular, either 60° C. during 10 minutes, followed by a drying at 35° C. during 110 minutes; or 50° C. during 30 or 40 minutes; or 48° C. during 120 minutes.

In accordance with another advantageous characteristic of the process according to the invention, the above-mentioned drying of the gel is carried out in a fluidized bed to obtain production of industrial amounts, namely at least one to several kilograms of gels and notably of beads, or particles.

In accordance with another characteristic of the process according to the invention, the above mentioned drying of the gel is carried out by means of a lyophilization technique in a vacuum, the temperature of lyophilization is preferably of the order of about −80° C.±10° C.

In accordance with another advantageous characteristic of the process according to the invention, the at least partially dehydrated gel obtained after the drying step of the said invention process is further preserved in a water vapor-tight packaging which is preferably maintained at a relatively low temperature, preferably at about 4° C.

In accordance with a preferred characteristic, this storage takes place under vacuum or in a controlled atmosphere very poor in oxygen and enriched in $CO_2$ or nitrogen.

In accordance with another advantageous characteristic of the process according to the invention, the microorganisms are selected from yeasts, in particular of the genus Saccharomyces, such as *Saccharomyces cerevisiae* and Schizosaccharomyces; and bacteria such as lactic bacteria.

In accordance with a second aspect, the present invention also relates to the use of at least partially dehydrated gels entrapping microorganisms mentioned above, for the preparation of fermented or re-fermented drinks as well as for the preparation of ethyl alcohol.

According to another aspect, the invention relates to a process for the production of fermented alcoholic drinks by a fermentation step carried out in the presence of immobilized microorganisms, wherein the improvement comprises preparing the immobilized microorganisms for the fermentation by:

(a) dispersing the microorganisms in a gellable polysaccharide solution;

(b) gelling the polysaccharide solution containing the microorganisms to form a gel enclosing the microorganisms;

(c) soaking the gel entrapping the microorganisms in a solution containing a sugar in a predetermined concentration and for a period of time sufficient to reach equilibrium, said predetermined sugar concentration being sufficient to obtain said gel containing said sugar in an amount ranging between at least 100 g/kg and less than 500 g/kg of gel;

(d) separating the equilibrated gel entrapping the microorganisms for the solution and recovering the gel;

(e) drying the gel to obtain an at least partially dehydrated gel;

(f) storing the at least partially dehydrated gel; and (g) re-hydrating the at least partially dehydrated gel entrapping the microorganisms; and (h) using the re-hydrated gel in the said fermentation step.

According to an advantageous embodiment of the above mentioned process for the production of fermented alcoholic drinks, the microorganisms entrapped in the re-hydrated gel obtained at said step (g) are reactivated before using them to perform said fermentation step.

In a further aspect, the invention relates to a process for a second fermentation of wine, that is called "prise de mousse", in the presence of immobilized yeasts in closed vessels, in particular bottles. Accordingly, the improvement of this process comprises preparing the immobilized yeasts for the second fermentation by:

(a) dispersing the yeasts in a gellable polysaccharide solution;

(b) gelling the polysaccharide solution containing the yeasts to form a gel entrapping the yeasts;

(c) soaking the gel entrapping the yeasts in a solution containing a sugar in a predetermined concentration and for a period of time sufficient to reach equilibrium, said predetermined concentration in sugar being sufficient to obtain said gel containing said sugar in an amount ranging between at least 100 g/kg and less than 500 g/kg of gel;

(d) separating the equilibrated gel entrapping the yeasts from the solution and recovering the gel;

(e) drying the gel to obtain an at least partially dehydrated gel;

(f) storing the at least partially dehydrated gel;

(g) re-hydrating the at least partially dehydrated gel entrapping the yeasts; and (h) using the re-hydrated gel in a second fermentation of wine According to a further aspect, the invention relates to an at least partially dehydrated gel containing viable microorganisms and a sugar in an amount ranging between at least 100 g/kg and less than 500 g/kg of the gel prior to dehydration.

According to the invention, said microorganisms entrapped in such an at least partially dehydrated gel exhibit an improved fermentation activity after rehydration.

According to an advantageous embodiment, the concentration in sugar ranges between at least 100 g/kg and less than 300 g/kg of the gel prior to dehydration.

According to another advantageous embodiment, the sugar content is at least 200 g/kg of the gel prior to dehydration.

Other embodiments of the gel according to the invention, clearly result from the above description relating to the other invention aspects and further from the herebelow detailed description of the invention including the examples, which are an integral part of the invention.

For all of the aspects of the invention, the rehydration and the reactivation may be performed according to well-known techniques. In the present invention, it is advantageous to perform this rehydration and reactivation as follows:

a) rehydration of the gel at least partially de-hydrated

The gel at least partially de-hydrated, which may be under the form of beads, is introduced in water.

However, to preserve the integrity of the gel, more particularly when it is an alginate gel, it is necessary either to acidify the aqueous medium, preferably to reach a pH of about 3.3, similarly to the pH of wine, by adding a lactic or tartaric acid, or to introduce in water a determined amount of cross-linking entity, which for an alginate gel is well-known to be calcium ions.

Accordingly, in the case of an alginate gel, calcium chloride will be used for instance at a concentration of 1 to 10 g/liter.

Preferably, it will be used an acid solution at pH of about 3.3.

The gel is maintained in this aqueous solution, at room temperature, for at least 1 hour, and if necessary, for a longer period of time up to 24 hours.

It is thereby obtained a rehydrated gel.

b) Reactivation step

This reactivation step is mainly advantageous or even necessary, when the microorganisms are beads to be used for a second fermentation of wine, so that the reactivation step is described herebelow with regard to reactivation of yeasts entrapped in a rehydrated gel, without being limited to the use of yeasts.

The rehydrated gel entrapping the yeasts, as obtained after the rehydration step (a) hereabove described, is suspended in an aqueous solution at an acid pH of about 3.3 as above described.

It is then added about 5% by weight of wine supplemented in sugar at a concentration of about 500 g/liter, said sugar being preferably sucrose.

The yeasts entrapped in the gel are maintained in this solution during about 24 hours, which duration can be prolonged up to 4 days.

During this reactivation step, samples can be taken to control the status of fermentary activity of the yeasts by means of the methylene blue test, which is also described in the present specification.

The invention makes it possible to achieve the previously mentioned non-obvious, unexpected technical results by solving the new technical problems previously set out by discovering, in an unexpected manner, that it was possible to preserve both the physical structure of the gels and the viability, and hence the fermentation activity, of the microorganisms if a predetermined concentration of sugar alone or combined with a low molecular weight polyol is used. Such a sugar is preferably selected from aldoses, ketoses and diholosides. More precisely, the aldose may be xylose or glucose, the ketose may be fructose, and the diholoside may be lactose or sucrose. The sugar presently much preferred is sucrose. Such a polyol is preferably selected from sorbitol, inositol and glycerol. The preferred polyol is glycerol.

With the invention, at least partially dehydrated gels are obtained which can easily be re-hydrated even after a prolonged period of storage.

The general conditions of the process for the preparation of the at least partially dehydrated gels including the microorganisms are the following:

a) a culture of the microorganisms is first grown in a suitable culture medium containing a carbon source, in particular carbohydrates, until the stationary phase is obtained, which corresponds in particular in the case of the yeasts to a low degree of budding or cell division, which is preferably lower than 5%.

b) All inclusion of the microorganisms present in the culture medium in an easily gellable or solidifiable polymer is carried out, as is standard practice.

This inclusion may be done by the standard technique of droplet formation so as to produce beads of gel enclosing the microorganisms.

Preferably, according to the invention, an inclusion with a double layer is carried out so as to produce a protective external layer or envelope of gel essentially free of cells of microorganisms.

c) The gel thus formed, in particular in the form of beads or fibers, is soaked in a solution containing a predetermined concentration of sugar.

This soaking is carried out until an equilibrium between the solution and the gel is obtained.

d) The drying of the thus soaked gel is then undertaken, at least partially, after separation of the latter from the solution containing the sugar by using any previously known suitable drying treatment.

It is possible to use, for example, the technique of the fluidized bed, lyophilization or even a desiccator containing a desiccant.

e) It is then possible to store the at least partially dehydrated gel enclosing a microorganism under vacuum or in an atmosphere composed essentially by $CO_2$ or nitrogen.

f) The particles can then be re-hydrated according to the methodology usually used in the case of the dried yeasts already on the market, for the purpose of using them.

g) Optionally, if required, the microorganisms entrapped in the re-hydrated gel are reactivated before further use.

Other aims, characteristics and advantages of the invention will become clearly apparent in the light of the explanatory description which follows made with reference to examples of the embodiment below in correlation with the appended figures. Naturally, these examples are given only as illustrations of the invention and hence should in no way be interpreted as constituting a limitation of the scope of the invention. Nevertheless, the examples are an entire part of the invention and any new feature, which can be drawn from the examples over any prior art, is a part of the invention as a general means thereof.

In the present description and the examples, all the percentages are given by weight, unless indicated otherwise.

Furthermore, except where indicated otherwise, the temperature is room temperature or is expressed in degrees Celsius, and pressure is atmospheric.

DESCRIPTION OF THE PREFERRED EMBODIMENTS

Example I

Preparation of at least partially dehydrated gels according to the invention by using a strain of *Saccharomyces cerevisiae* as microorganism.

1. Microorganism strain

In this example, a strain of *Saccharomyces cerevisiae* is used as microorganisms strain.

2. Culture of the microorganisms

A wine supplement with 50 g/l sucrose as hydrocarbon source is used as culture medium.

The yeasts are cultivated in conical flasks on a shaking platform at 16° C. and harvesting is done after 4 days of culture at a stage at which the microorganisms have a low degree of budding, preferably not exceeding 5%.

The culture medium is centrifuged so as to separate the microorganisms which are placed in suspension in an aqueous solution.

3. Preparation of gels containing the microorganism cells

It is at first prepared an aqueous solution of sodium alginate by dissolving sodium alginate (available on the market under the trademark "CECA SG 1100") in de-mineralized water at room temperature at a concentration of 15 g/liter, thereby obtaining a final solution of 1.5% in sodium alginate.

After leaving overnight for a static degassing, this alginate is used for the preparation of alginate gels in a form of beads having a double alginate layer, namely an inner alginate layer and an outer alginate layer.

The outer alginate layer is prepared by diluting the above alginate basic solution with de-mineralized water in order to obtain a concentration of 11.5 g/liter in alginate, or 1.15% by weight.

The internal alginate, namely the alginate solution, which will be used to prepare the internal layer of the beads is prepared by admixing the aqueous suspension containing the microorganism cells, as prepared above, with a part of the basic alginate solution. The volume is set in order to obtain a suspension of cells in the concentration of $1.2 \times 10^8$ to $1.2 \times 10^9$ cells per milliliter and the alginate concentration of 11.5 g/liter, namely 1.15% by weight, identical to the concentration of the internal alginate aimed for obtaining the internal layer of the gels.

4. Production of the double layer gels in the form of beads having an internal layer containing the microorganism cells and an external layer free of microorganism cells The preparation of the double layer gels is performed in accordance with example II as set forth in U.S. Pat. No. 5,389,532 by using two concentric tubes as shown in FIG. 4 of U.S. Pat. No. 5,389,532. These tubes comprise a central axial tube, into which the internal alginate, namely the alginate containing the microorganism cells in suspension, is introduced. In the external tube, concentric with the internal tube, the external alginate solution, namely the alginate solution devoid of cells of microorganisms is introduced alone.

The internal and external alginates are pumped simultaneously in said two concentric tubes and reach the outlet, which is vibrated with the help of a vibrator to obtain a disruption of the continuous flow running from the outlet of the two concentric tubes and generate droplets having a pre-determined shape and diameter.

In this way, droplets are generated, which consist of an external alginate layer free or essentially free of microorganism cells surrounding an internal alginate layer or core containing the microorganism cells, said droplets being therefore double layer droplets.

These droplets fall into a cross-linking bath which consists of an aqueous solution of calcium chloride having a concentration which may vary between 20 and 200 g/liter. The calcium ions perform an instantaneous cross-linking of the alginate, thereby forming double layer alginate gels, here in the form of beads.

In the following seconds, the beads are separated from the cross linking bath. The cross-linking continues automatically since a thin layer of cross-linking solution remains at the surface of the beads, which is allowed to stay about 15 minutes prior to performing any washing.

5. Washing and Storage

The cross-linked beads are washed during 15 minutes with tap water in order to remove the excess of calcium. The beads are then stored in an aqueous solution of tartaric acid at a concentration of 0.5 g/liter, while using one volume of tartaric acid solution for one volume of beads, at a temperature of about 4° C.

During such a storage, a sugar feed is performed dropwise to feed the microorganism cells. The duration of this storage phase ranges between one and four days and does not change the behavior of the microorganism cells for the latter step, notably for the drying. The produced wet beads have a diameter ranging between 2 and 2.5 mm and the number of microorganism cells per bead ranges between 0.5 and $5.10^6$.

6. Dehydrating Treatment of the Beads

A—Osmotic dehydration

This osmotic dehydration is an integral part of the present invention and is performed as follows:

the alginate beads removed from the storage solution are smoothly shaken in order to stop any droplets of the storage solutions before their introduction into a dehydrating aqueous solution containing a sugar and/or a low molecular polyol, which is the above mentioned soaking solution according to the present invention, at a ratio of 3 volumes of beads for 3 to 10 volumes of dehydrating solution. The medium is permanently stirred. After 30 minutes, equilibrium is usually reached, which can be noted by observing the beads falling onto the bottom of the reservoir. The beads are then shaken to remove the remaining osmotic dehydration solution and are then dried as set forth below.

It has to be noted that at the equilibrium, the sugar concentration and the polyol concentration in the osmotic dehydrating solution are essentially the same as in the equilibrated gel. For this reason, it can be admitted that the concentration values reported in the tables I to X in the following description for the sugars and glycerol refer as well to the osmotic dehydrating or soaking aqueous solution as to the equilibrated gel before drying.

In the present tests, three osmotic dehydration agents are tested: sucrose, glucose and glycerol, each of them at varying concentrations, as reported in table I hereinafter. For this purpose, the beads are sub-divided into 7 samples of 300 g each, labeled respectively number 1 to number 7, as set forth in table I hereinafter.

The beads are added in the osmotic dehydrating solution at a rate of 300 g of beads per liter of osmotic dehydration solution providing a total volume of about 1300 cm3 which reaches a concentration in sugar and/or polyol per liter as set forth in table I hereinafter. The beads are left in the dehydrating solution for 30 minutes.

Then, the drying of the beads is performed as set forth hereinafter.

B—Drying of the beads

The drying of the beads, which have been submitted to the above said osmotic dehydration solution, is performed in a hot air flow, the temperature of which cannot be precisely controlled, but which varies between 45 and 55° C.

In a laboratory, when the weight of the samples does not exceed about 300 g, as is the present case, a dryer with a fluidized bed is used which is commercially available under the trademark of RETSCH® type TGI. With such a fluidized bed dryer, the air flow rate is 100 m3/hour at a temperature of about 50° C.

The period of time of the drying ranges between 30 and 45 minutes, with the exception of sample No.5, for which the period of time of drying was extended for one hour due to the difficulty in drying the beads resulting from the high concentration in sugar, namely glucose used for the osmotic dehydration and which is present in the beads.

7. Measurement of the cell activity by the methylene blue test

The cell activity is measured by the methylene blue test.

The methylene blue test is well-known to those skilled in the art of yeast in the characterization of the fermentation activity of the yeast cells. When the yeast cells are active for fermentation, they are not colored, whereas those cells which have been damaged or killed by the drying process are stained by methylene blue. This staining test is regarded by those skilled in the art as a reliable way of characterizing the percentage of living cells and is applied here to test the activity of the cell population in dried beads.

This staining was performed twice for each sample. The observation and count of the living cells was performed by microscopic examination on a Thoma cell, as well-known to those skilled in the art. The microscopic examination is performed after 5 minutes of contacting the beads with a sodium citrate solution at 20 g/l containing methylene blue at a concentration of 0.1 g/l. The sodium citrate solution dissolves the alginate gel to liberate the cells before staining by methylene blue.

The fermentation activity of the microorganism cells after osmotic dehydration and drying has been tested by the methylene blue test and results are reported in table I hereinafter.

TABLE I

Testing of the activity of the microorganism cells after osmotic dehydration and drying

| Sample N* | Sucrose g/l | Glucose g/l | Glycerol g/l | Total Sugar + Polyol g/l | Activity of cells after drying in % t = 0 |
|---|---|---|---|---|---|
| 1 | 75 | | | 75 | 33 |
| 2 | 220 | | | 220 | 50 |
| 3 | | 75 | | 75 | 38 |
| 4 | | 220 | | 220 | 52 |
| 5 | | 380 | | 380 | 27 |
| 6 | 150 | | 95 | 245 | 52 |
| 7 | | 150 | 95 | 245 | 50 |

It must be noted that the activity of the microorganism cells is considered to be satisfactory after drying, as evidenced by the methylene blue method, when at least about 50% of the microorganism cells are active.

Accordingly, it results from the tests results reported on table I that:

a) when the content of sugar alone is lower than 100 g/liter, namely 75 g/liter in samples No.1 and No.3, respectively for sucrose and glucose, a percentage of activity of the microorganism cells is obtained which is well below 50%, namely below 40%;

b) for sample No.5, due to its high glucose concentration, namely 380 g/liter, the drying of the beads was very difficult and required an extended drying period, which at the temperature of drying used was detrimental to the activity of the microorganism cells. It is most probable that using a lower drying temperature during a longer time could avoid this drawback.

c) When the amount of sugar alone or combined with a low molecular weight polyol such as glycerol higher than 100 g/liter is used, namely around 150 g or 220 g, a good protection of the microorganism cells is achieved, which is at least 50% of the cells, it is believed that an improvement in the drying conditions, notably by precisely controlling the temperature of the drying air, would further improve the results.

d) Since the microorganism cells are microorganisms obtained by cultivation in alcoholic medium which is used on an industrial scale, and notably for the preparation of sparkling wine, and notably champagne, which are detrimental for the viability of the cells, it is obtained a god protection of the microorganism cells is obtained.

It will be seen in the following examples that when the microorganism cells are cultivated in a non-alcoholic medium, the preservation of the activity of the microorganism cells is much better.

These dried beads constituting samples No.1 to No.7 are then used for the preparation of sparkling wine, as set forth hereinafter.

8. Further testing activity of cells after rehydration and reactivation

The above 7 samples, which have been dried, are tested for the preparation of sparkling wine.

Each sample is either used directly in wine, or after a simple rehydration step in acidified water or again after rehydration and reactivation in wine supplemented with sugar.

A—Rehydration

The rehydration consists in dipping the dried cells in water acidified with lactic or tartaric acid in order to obtain a pH similar to that of wine, namely 3.3.

During the rehydration, the cells recover a fermentary activity and perform the consumption of a part of the sugar used as osmotic dehydration agent. The minimum duration of this hydration phase, which is performed at room temperature, is of 1 hour and can be extended up to 24 hours.

B—Reactivation

Reactivation of the cells, which have been re-hydrated as emphasized above, is in this example performed by dipping the re-hydrated beads in wine supplemented with sugar at a concentration ranging from 10 g/l to 25 g/l for two to four days.

The staining is performed twice for each sample, either immediately after drying (t=0), or after 24 hours of rehydration (activity measured after rehydration), or after 4 days of rehydration/reactivation time; the duration of rehydration being 1 day, the reactivation time being of 3 days (activity after reactivation reported above in table II).

These tests are reported in Table II hereinafter:

Wine supplemented with 26 g/l of sucrose is poured into a 0.75 liter bottle. The dosis of beads is tested, of about 3 g is added to the wine. This operation is generally called as "tirage", which is a French word used worldwide by the sparkling wine makers using the second fermentation in bottles. The bottle is closed tightly with an cover and capsule. The bottle is stored in a cellar which has a temperature of 12° C. The cells having a proper fermentation activity will perform the bio-conversion of sugar into alcohol with the simultaneous formation of carbon dioxide, which is usually named as second fermentation, "champagnization" or "prise de mouse". This fermentation activity can be followed simply by measuring the increase of pressure in the bottle and/or by determining analytically the lowering of the sugar concentration.

This second fermentation step is lasting on average 6 weeks, but can be extended up to 6 months.

In the present case, for the preparation of sparkling wine, tests are performed for each sample under three variations, namely either with dried beads directly added to the wine,

TABLE II

Activities of the microorganism cells after drying the beads prior to second fermentation for obtaining sparkling wine

| Sample N* | Sucrose g/l | Glucose g/l | Glycerol g/l | Total Sugar + Polyol g/l | Activity of cells after drying in % | Activity of cells after rehydration in % | Activity of cells after reactivation in % |
|---|---|---|---|---|---|---|---|
| 1 | 75 | | | 75 | 33 | 0 | 28 |
| 2 | 220 | | | 220 | 50 | 30 | 44 |
| 3 | | 75 | | 75 | 38 | 0 | 43 |
| 4 | | 220 | | 220 | 52 | 8 | 25 |
| 5 | | 380 | | 380 | 27 | 27 | 27 |
| 6 | 150 | | 95 | 245 | 52 | 7 | 35 |
| 7 | | 150 | 95 | 245 | 50 | 42 | 67 |

It results from table II above which completes the activity testing reported in table I that rehydration and reactivation is an acidified medium, such as acidified water or sugared wine, has a rather detrimental effect on the apparent viability refermentation activity of the cells, as shown by the methylene blue tests.

9. Second fermentation of wine or froth uptake

The second fermentation of wine or froth uptake is performed as follows:

reported in table III hereinafter under the heading "Tirage with dried beads, t=17 days"; another part was added to the wine after a rehydration step in acidified water and the results are reported in table III under heading "Tirage with re hydrated beads, t=16 days" and the remaining part of each sample was re-hydrated and reactivated and is reported in table III under the heading "Tirage with re-hydrated and reactivated beads, t=13 days". The initial sugar content is 26 g/liter.

TABLE III

Production of sparkling wine with yeast cells in gel beads after drying, rehydration and/or reactivation (measure of remaining sugar at t = 17, 16 or 13 days)

| Sample N° | Sucrose g/l | Glucose g/l | Glycerol g/l | Total Sugar + Polyol g/l | Tirage with dried beads t = 17D* | Bottling with re-hydrated beads t = 16D* | Tirage with re-hydrated and reactivated beads t = 13D* |
|---|---|---|---|---|---|---|---|
| 1 | 75 | | | 75 | No pressure | 25.5/0.03 | 20.8/0.4 |
| 2 | 220 | | | 220 | | 21.3/0.29 | 23.2/0.21 |
| 3 | | 75 | | 75 | | 22.3/0.23 | 21/0.38 |
| 4 | | 220 | | 220 | | 21.3/0.29 | 20.3/0.44 |
| 5 | | 380 | | 380 | | 23.1/0.18 | 21.1/0.38 |

TABLE III-continued

Production of sparkling wine with yeast cells in gel beads after drying, rehydration and/or reactivation (measure of remaining sugar at t = 17, 16 or 13 days)

| Sample N° | Sucrose g/l | Glucose g/l | Glycerol g/l | Total Sugar + Polyol g/l | Tirage with dried beads t = 17D* | Bottling with re-hydrated beads t = 16D* | Tirage with re-hydrated and reactivated beads t = 13D* |
|---|---|---|---|---|---|---|---|
| 6 | 150 | | 95 | 245 | | 17/0.56 | 18.9/0.55 |
| 7 | | 150 | 95 | 245 | | 18.6/0.46 | 19.1/0.53 |

* = the results are expressed first in terms of concentration of sugar, expressed in g/l, remaining in the bottle, after a fermentation time of 17 days for the dried beads, 16 days for the re-hydrated beads, or 13 days for the re-hydrated and reactivated beads; and the second value expresses the fermentation speed calculated by subtracting the measured remaining sugar concentration from the initial sugar value, which was 26 g/l, divided by the number of days of fermentation. For instance, with the first value of residual sugar concentration of 25.5 g/l, the calculation gives:

$$\frac{26 - 25.5}{16} = 0.03 \text{ g/l/day.}$$

It has to be noted that fermentation speed has been observed to be essentially constant during substantially the first three weeks of second fermentation in closed bottles. Accordingly, there is no substantial difference between speed measured at 13 days or at 16 days. Consequently, the expression of the result in fermentation speed is preferred and is reliable.

For a conventional method of production of sparkling wine, with free yeast cells, it was found that the speed of conversion of sugar into alcohol by the yeast is in an average about 0.5 g/l/day.

The closest results to this average fermentation speed of the conventional method are obtained with samples No.6 and No.7, which were treated with the osmotic dehydrating solution containing an association of a sugar with a low molecular weight polyol, namely either sucrose or glucose with glycerol, since about 7 g have been consumed, namely converted into alcohol.

These results demonstrate that the presence of glycerol, associated with a sugar, unexpectedly allows the yeasts entrapped in a gel rehydrated according to the process of the invention to recover a normal fermentation activity.

Furthermore, unexpectedly again, this association is so successful that the reactivation of the yeast after the rehydration step appears quite unnecessary.

In fact, it appears clearly from the comparison of the fermentation speeds between the "tirage" with beads rehydrated only and the "tirage" with rehydrated and reactivated beads set forth in the table III above, that reactivation of the yeasts is essentially required when the fermentation activity of the yeast cells has been significantly impaired by the drying process. That is particularly obvious for the sample No.5, for which the fermentation activity of the yeast cells have been dropped to 27% after the drying step, as shown in table I, due to a too long drying time.

Furthermore, for the production of sparkling wine, it appears that the direct addition of the dried beads, which were not re-hydrated, failed. No production of carbon dioxide has been observed, namely no second fermentation occurs in the bottles. For the second part of the present test, refermentation of the wine is continued for six months from the date of "tirage" (t=0), to ensure a complete refermentation. After this period, measurements are performed. The results are reported in table IV.

TABLE IV

Second fermentation of wine after six months Turbidity and remaining sugar content in wine

| Sample N* | Sucrose g/l | Glucose g/l | Glycerol g/l | Total Sugar + Polyol g/l | Tirage with dried beads | Tirage with re-hydrated beads Turb./Remaining Sugar g/l | Tirage with re-hydrated and reactivated beads Turb./Remaining Sugar g/l |
|---|---|---|---|---|---|---|---|
| 1 | 75 | | | 75 | Turbidity | 4.4/2.8 | 0.7/1.1 |
| 2 | 220 | | | 220 | >5 | 0.85/1.3 | 0.45/1 |
| 3 | | 75 | | 75 | | 0.26/2.6 | 0.6/2.7 |
| 4 | | 220 | | 220 | | 0.22/2.7 | 0.2/2.7 |
| 5 | | 380 | | 380 | | 0.25/2.7 | 0.2/1.7 |
| 6 | 150 | | 95 | 245 | | 0.30/2.2 | 0.2/1.7 |
| 7 | | 150 | 95 | 245 | | 0.12/2.2 | 0.12/1.8 |

Some turbidity in sparkling wine refermented by yeasts entrapped in gel beads appears essentially when, in spite of the immobilization of the yeast cells in the matrix of the gel, some of them proliferate in wine outside of the gel. That may occur when the structure of the gel is impaired at such an extent that its mechanical qualities become insufficient.

It is generally considered that the turbidity level of a sparkling wine of high quality, and especially Champagne, must not rise over the value of 1.0.

Turbidity is according to the invention measured by means of a turbidimeter working according to the principle of diffraction of light ray by the object to be analyzed.

The values are expressed in units F.T.U, namely Formazin Turbidity Units. This method of appreciation of the optical quality of liquids is used in oenology as well as to appreciate the quality of a drinkable water. This method is also disclosed by Stump V. I., et al., in J. Amer. Water Works Assoc. (1979) 71 (6), 338–342.

From the table IV above, it appears clearly that the samples of the tirage with dried beads put directly in the wine, the turbidity of which is higher than 5, do not give any acceptable result.

Likewise the sample No.1 in the tirage with rehydrated beads does not give good result in terms of turbidity. It seems that probably the sugar content in the gel, which raised at only 75 g/l, was insufficient for protecting the structure of the gel, and hence for preserving its integrity.

In view of the foregoing, it appears that surprisingly, performing an osmostic dehydration by dipping beads entrapping microorganism cells, into a solution of sugar and/or polyol at a concentration higher than 100 g/liter and lower than 500 g/liter and even lower than 400 g/liter, provide unexpected, non-obvious results for one skilled in the art of the second fermentation of wine by reaching a low turbidity value combined with a high consumption of sugar, in particular when the beads have been reactivated prior to bottling the wines.

Example II

In this example, essentially the same procedure of manufacture of the dehydrated beads is performed as in example I, except that the microorganism cells of the *Saccharomyces cerevisiae* strain have been cultivated in fed-batch in a malt Wickerham aqueous medium with glucose as hydrocarbon source, instead of wine as used in example I.

Furthermore, after performing the osmotic dehydration, the beads are dried in a semi-industrial fluidized bed providing an air flow which can be set from 0 to 3 meters per second, a temperature which can be set between 0 and 150° C. and a drying capacity in average of 3 to 4 kg.

The drying conditions have been optimized for 3 kg of beads in this fluidized bed to be set at:

air speed: 2.7 meters/second;

drying time: 2 hours;

drying temperature: 60° C. during 10 minutes for which the bead temperature does not exceed 40° C., then 35° C. for the remaining drying time.

In this example, a new series of 19 samples is performed with an amount of sugar varying from about 150 to about 400 g/liters alone or combined with a low molecular weight polyol, namely glycerol with a total amount of sugar plus polyol lower than 500 g.

Furthermore, for samples No.11 to No.14, a surfactant is further added as drying protecting substance, for the yeasts, namely sorbitan monostearate and is mentioned in table V with the letter S.

The test results are reported in table V hereinafter in which the water activity Aw has been measured, as well as the percentage of activity of the microorganism cells after drying, namely at t=0, with methylene blue as staining agent and also after two months at 25° C.

TABLE V

| Drying | Sucrose g/l | Glycerol g/l | Glucose g/l | Total Sugar + Polyol g/l | Aw | % of activity of cells t = 0 | % of activity of cells 2 months 25° C. |
|---|---|---|---|---|---|---|---|
| 1 | 190 | | | 190 | 0.49 | 87 | 20 |
| 2 | 250 | | | 250 | 0.51 | 84 | 20 |
| 3 | 310 | | | 310 | 0.52 | 84 | 20 |
| 4 | 190 | 80 | | 270 | 0.42 | 90 | 30 |
| 5 | 190 | 125 | | 315 | 0.36 | 80 | 10 |
| 6 | 190 | 155 | | 345 | 0.41 | 94 | 20 |
| 7 | 125 | | 125 | 250 | 0.5 | 75 | 20 |
| 8 | | 115 | 125 | 235 | 0.36 | 99 | 20 |
| 9 | 125 | 115 | 125 | 365 | 0.37 | 90 | 40 |
| 10 | 190 | 125 | 190 | 495 | 0.43 | 90 | 40 |
| 11-1 + S | 190 | | | 190 | 0.46 | 97 | 40 |
| 12 = 5 + S | 190 | 115 | | 305 | 0.36 | 93 | 40 |
| 13 = 8 + S | | 115 | 125 | 240 | 0.36 | 92 | 30 |
| 14 = 10 + S | 190 | 115 | 190 | 495 | 0.42 | 91 | 30 |
| 15 | 190 | 80 | 65 | 335 | 0.4 | 80 | 20 |
| 16 | 65 | 40 | 95 | 240 | 0.38 | 85 | 25 |
| 17 | 125 | 155 | | 280 | 0.39 | 85 | |
| 18 | 135 | 155 | | 290 | 0.36 | 75 | |
| 19 | 155 | 245 | | 400 | 0.38 | 95 | |

It is to be noted that storage tests at 4° C. have also been performed and that the loss of activity of the cells after 2 months is at the maximum of 10%.

The following conclusions can be drawn from table V:

A—Influence of the concentration in sucrose

The influence of concentration in sucrose is shown in table VI hereinafter:

TABLE VI

| Drying | Sucrose g/l | Aw | % of activity of cells t = 0 | % of activity of cells - 2 months at 25° C. |
|---|---|---|---|---|
| 1 | 190 | 0.49 | 87 | 20 |
| 2 | 250 | 0.51 | 84 | 20 |
| 3 | 310 | 0.52 | 80 | 20 |

Table VI shows that even at a lower content in sucrose of 190 g/l a very good fermentation activity is preserved after drying, an also after a 2 months storage at 25° C. Water activity Aw is also acceptable at about 0.50.

B—Influence of addition of a low molecular weight polyol, here glycerol

The influence of addition of a low molecular weight polyol, here glycerol, is reported in table VII hereinafter.

TABLE VII

| Drying | Sucrose g/l | Glycerol g/l | Aw | % of activity of cells t = 0 | % of activity of cells 2 months 25° C. |
|---|---|---|---|---|---|
| 1 | 190 | 0 | 0.49 | 87 | 20 |
| 4 | 190 | 80 | 0.42 | 90 | 30 |
| 5 | 190 | 125 | 0.36 | 80 | 10 |
| 6 | 190 | 155 | 0.41 | 94 | 20 |

Glycerol has a very favorable action as well on the lowering of water activity as on the preservation of activity after the dehydration treatment for each sample, but sample No.5, at a less extent, due to an overheating during the drying step.

C—Influence of addition of glucose

The substitution of a part of sucrose by glucose is now shown more clearly in table VIII hereinafter.

TABLE VIII

| Drying | Sucrose g/l | Glycerol g/l | Glucose g/l | Total g/l | Aw | % of activity of cells t = 0 | % of activity of cells 2 months 25° C. |
|---|---|---|---|---|---|---|---|
| 2 | 250 | | | 250 | 0.51 | 84 | 20 |
| 7 | 125 | | 125 | 250 | 0.5 | 75 | 20 |
| 8 | | 115 | 125 | 235 | 0.36 | 99 | 20 |
| 9 | 125 | 115 | 125 | 365 | 0.37 | 90 | 40 |
| 10 | 190 | 115 | 190 | 495 | 0.43 | 90 | 40 |
| 15 | 190 | 80 | 65 | 335 | 0.4 | 80 | 20 |
| 16 | 65 | 40 | 95 | 210 | 0.38 | 85 | 25 |

It results from table VIII that the substitution of a part of sucrose by glucose, as made in sample No.7 as compared to sample No.2, provides a slight deterioration of the fermenting activity without improving the lowering of water activity Aw.

In the opposite, an association glucose/glycerol as examplified by sample No.8, reaches both the preservation of the cell activity and the lowering of the water activity Aw. The triple association of sucrose, glucose and glycerol, as shown by samples No.9 and No.10, provides the best results particularly for obtaining a preservation of the cell activity for a long period of storage at room temperature.

It has to be noted again that surprisingly the best results are obtained with the tests using a combination with glycerol at an amount of 115 g/l.

Based on samples Nos. 5, 8, 12, 13, 17, 18, 19, an association of sugar and polyol is sufficient to obtain a low water activity Aw, the best results of this twofold association being obtained with those based on sucrose/glycerol and glucose/glycerol.

Experiments 17, 18 and 19 enable confirming the efficiency of the combination of sucrose and glycerol as osmotic dehydrating agent as shown in table IX hereinafter.

TABLE IX

| Drying | Sucrose g/l | Glycerol g/l | Glucose g/l | Total g/l | Aw | % of activity of cells t = 0 |
|---|---|---|---|---|---|---|
| 17 | 125 | 155 | | 280 | 0.39 | 85 |
| 18 | 135 | 155 | | 290 | 0.36 | 75 |
| 19 | 155 | 245 | | 400 | 0.38 | 95 |

It results from table IX that with a higher concentration of glycerol, the highest cell activity is obtained with a low water activity Aw.

D—Influence of the presence of a drying protecting agent

Influence of drying protecting agent for yeast, like surfactant, is shown in table X hereinafter.

TABLE X

| Drying | Sucrose g/l | Glycerol g/l | Glucose g/l | Total g/l | Aw | % of activity of cells t = 0 | % of activity of cells 2 months 25° C. |
|---|---|---|---|---|---|---|---|
| 1 | 190 | | | 190 | 0.49 | 87 | 20 |
| 11 = 1 + S | 190 | | | 190 | 0.46 | 97 | 40 |
| 5 | 190 | 125 | | 315 | 0.36 | 80 | 10 |
| 12 = 5 + S | 190 | 125 | | 315 | 0.36 | 93 | 40 |
| 8 | | 115 | 125 | 240 | 0.36 | 99 | 20 |
| 13 = 8 + S | | 115 | 125 | 240 | 0.36 | 92 | 30 |
| 10 | 190 | 115 | 190 | 495 | 0.43 | 90 | 40 |
| 14 = 10 + S | 190 | 115 | 190 | 495 | 0.42 | 91 | 30 |

It results from table X that the drying protecting agent for yeasts, such as a surfactant, preserves the cell activity, particularly in samples 11 and 12. The protecting action is clearly apparent when measuring the residual cell activity after a two months storage at room temperature.

Example III

Comparative tests demonstrating the superiority of the invention over the technique described in Cheetham European patent application No. 65,376.

Wet beads, namely calcium alginate gel containing yeast cells, were initially prepared for treatment in accordance with the Cheetham technique and that of the present invention. The wet beads were prepared according to a procedure well known to those skilled in the art, basically as set forth in Example II of the invention, as follows:

After cultivating yeasts of a strain of *Saccharomyces cerevisiae* as disclosed in Example II, the culture medium was centrifuged so as to separate the microorganisms which are suspended in an aqueous solution. The suspension was then mixed with an aqueous solution of sodium alginate "CECA SG 800" in order to obtain a final solution containing 1.5% by weight alginate. The mixture was then pumped and added to a solution of 0.4 M $CaCl_2$ at a pH of 7.

After 30 minutes of contact, the hardened particles in the form of beads of calcium alginate enclosing the cells of *Saccharomyces cerevisiae* microorganism, were rinsed with distilled water. The hardened particles had a mean diameter of 2.2 millimeters and contained about $5 \times 10^8$ cells of microorganisms/ml.

The thus formed wet beads were then used in the following comparative test of the Cheetham technique and the invention process:

A—A first part of the wet beads prepared as described above was directly incubated at room temperature in pure glycerol for 6 days. The resulting beads, beads "B1", were then hydrated and reactivated in a hydration and reactivation medium comprising an aqueous solution containing 200 g/l of sucrose and 600 mg/l of ammonium dihydrogen phosphate at pH 3.2, to form beads "B'1". The diameter of the beads B'1 appeared to be 2.08 mm. The foregoing procedure generally conforms with that described in Example 1 of the Cheetham European application.

B—A second part of the wet beads was dried in air at a temperature of 45° C. for a period of time sufficient to decrease the bead volume by about 39%. The dried beads were then incubated in pure glycerol for 6 days to obtain dried beads "B2", which were then hydrated and reactivated in the same sucrose aqueous medium to provide re-hydrated and reactivated beads "B'2". The diameter of beads B'2 was 2 mm.

The foregoing procedure generally conforms with that described in Example 2 of the Cheetham European application.

C—A third part of the wet beads was incubated in an aqueous sucrose solution containing 500 g per liter of sucrose until equilibrium was reached (observed when the beads settled in the aqueous sucrose solution). The equilibrated beads were then dried in air at 40° C. until the volume of the beads was reduced by 53% to provide dried beads "B3". The dried beads B3 were then re-hydrated and reactivated in the same hydration and reactivation aqueous sucrose medium to provide re-hydrated and reactivated beads "B'3". The foregoing procedure generally conforms with that described previously in the specification of the present invention.

All the re-hydrated and reactivated beads, respectively B'1, B'2 and B'3, were submitted to a comparative viability test by staining with methylene blue. Such a test is well known to those skilled in the art of yeast to characterize the activity of the yeast cells. When the yeast cells are active, they are not colored, whereas those cells which have been damaged or killed by the drying process are stained by the methylene blue.

This staining test is regarded by those skilled in the art as a reliable way to characterize the percentage of active cells after rehydration/reactivation.

This staining was performed twice for each group of beads B'1, B'2 and B'3, respectively, for a period of time of either 20 hours of reactivation or of 48 hours reactivation. The observation and count of the active cells was performed by microscopic examination on a THOMA cell, as well known to those skilled in the art. The test results are reported in Table XI below:

TABLE XI

Viability of yeast cells (**) (Staining by "methylene blue")
Percentage of active cells after rehydration/reactivation

| | TIME IN THE REACTIVATION MEDIUM | | |
|---|---|---|---|
| | After 20 hours | After 48 hours | |
| | Rate of viability | Rate of viability | Increase of Biomass |
| B'1 | 2 | 48 | no significant variation |
| B'2 | 37 | 70 | two fold |
| B'3 | 55 | 85 | five fold |

(**) The initial rate of viability (for initial wet fresh beads) was 88%.

It will be seen from Table XI after 20 hours of reactivation time, beads B'1 prepared according to Example 1 of the Cheetham application contained only 2% of active cells, which percentage increased to 48% after an additional 28 hours with no significant variation of the biomass. Even after 48 hours, there were still 52% of yeast cells which remained inactive. The lack of increase in biomass further indicates that the cells had been impaired by the incubating treatment in pure glycerol for 6 days.

With regard to beads B'2, the test results show that 37% of the cells were alive after 20 hours of reactivation time and 70% were alive after 48 hours with a two fold increase in biomass. This shows that the provision of drying prior to incubating into glycerol improved the viability of the yeast cells.

On the other hand, with the beads B'3 prepared in accordance with the invention process, a further unexpected increase in viability of the cells appeared even after 20 hours of reactivation time, by providing a percentage of living cells of 55% (which is an increase of more than 50% relative to beads B'2). Additionally, the percentage of living cells in beads B'3 was 85% after 48 hours with five-fold increase of biomass. When compared to the results provided with beads B'2, these results demonstrate the very high performance of the yeast cells in culture when prepared according to the process of the invention.

Based upon the results of the foregoing comparative test, it is clear that the process of the invention unexpectedly provides superior positive results relative to the prior art process disclosed in the Cheetham application, these results are believed to be non-obvious to one skilled in the art prior to the invention.

I claim:

1. An at least partially dehydrated polysaccharide gel comprising:
    viable microorganisms, a sugar selected from the group consisting of xylose, glucose, fructose, lactose and sucrose in an amount of at least 100 g/kg and less than 300 g/kg of the gel prior to dehydration, and a polyol selected from the group consisting of sorbitol, inositol and glycerol in an amount of at least 30 g/kg of the gel prior to dehydration, wherein said microorganisms exhibit an improved viability after rehydration as compared with a polysaccharide gel containing said viable microorganisms, which has been at least partially dehydrated in the absence of said sugar, and after the rehydration.

2. The gel of claim 1, wherein said sugar is present in an amount of at least 200 g/kg of the gel prior to dehydration.

3. The gel of claim 1 in the form of beads.

4. The gel of claim 3, wherein the beads have a double layer structure comprising an outer layer essentially devoid of the microorganisms and an internal core containing the microorganisms.

5. The gel of claim 1, wherein the gel further comprises a protecting substance in a sufficient concentration to improve the viability of the microorganisms during a drying step and to improve a fermentation activity of said microorganisms after the rehydration.

6. The gel of claim 5, wherein said protecting substance is a non-ionic surfactant.

7. The gel of claim 6, wherein said non-ionic surfactant is a sorbitan ester with a fatty acid.

8. The gel of claim 7, wherein said sorbitan ester is a sorbitan monostearate.

9. The gel defined in claim 1, wherein the polyol is provided from a soaking solution containing the polyol in an amount of at least 30 g/l to less than 500 g/l.

10. An at least partially dehydrated polysaccharide gel comprising: viable microorganisms, a sugar selected from the group consisting of glucose and sucrose in an amount of at least 100 g/kg and less than 300 g/kg of the gel prior to dehydration, and a polyol selected from the group consisting of sorbitol, inositol and glycerol in an amount of at least 30 g/kg of the gel prior to dehydration, wherein said microorganisms exhibit an improved viability after rehydration as compared with a polysaccharide gel containing said viable microorganisms, which has been at least partially dehydrated in the absence of said sugar, and after the rehydration.

11. An at least partially dehydrated polysaccharide gel comprising: viable microorganisms, a sugar selected from the group consisting of glucose and sucrose in an amount of at least 100 g/kg and less than 300 g/kg of the gel prior to dehydration, and glycerol in an amount of at least 50 g/kg of the gel prior to dehydration, wherein said microorganisms exhibit an improved viability after rehydration as compared with a polysaccharide gel containing said viable microorgansims, which has been at least partially dehydrated in the absence of said sugar, and after the rehydration.

12. The gel of claim 11, wherein the glycerol is present in an amount of at least 50 g/kg to less than 200 g/kg prior to rehydration.

13. The gel of claim 11, further comprising a non-ionic surfactant comprising a sorbitan ester with a fatty acid as a protecting substance.

14. The gel of claim 11, further comprising sorbitan monostearate as a protecting substance in an amount of about 1 g to 100 g of dry microorganisms.

15. The gel of claim 11, wherein said microorganisms are selected from bacteria and yeasts.

16. The gel of claim 15, wherein said yeast is *Saccharomyces cerevisiae*.

17. The gel of claim 15, wherein said bacteria is a lactic bacteria.

18. An at least partially dehydrated polysaccharide gel comprising:
    viable microorganisms and a sugar selected from the group consisting of glucose and sucrose in an amount of at least 100 g/kg and less than 300 g/kg of the gel prior to dehydration, said microorganisms exhibiting an improved viability after rehydration as compared with a polysaccharide gel containing said viable microorganisms, which has been at least partially dehydrated in the absence of said sugar, and after the rehydration; and glycerol in an amount of at least 50 g/kg to less than 200 g/kg.

19. The gel defined in claim 18, further comprising sorbitan monostearate in an amount of about 1 g to 100 g of dry yeast.

20. An at least partially dehydrated polysaccharide gel comprising viable microorganisms, a sugar selected from the group consisting of xylose, glucose, fructose, lactose and sucrose in an amount of at least 100 g/kg and less than 300 g/kg of the gel prior to dehydration, and a polyol selected from the group consisting of sorbitol, inositol and glycerol in an amount of at least 30 g/kg of the gel prior to dehydration, wherein said microorganisms exhibit an improved viability after rehydration as compared with a polysaccharide gel containing said viable microorganisms, which has been at least partially dehydrated in the absence of said sugar, and after the rehydration, which has been produced by a process comprising:

(a) dispersing the microorganisms in a gellable polysaccharide solution;

(b) gelling the polysaccharide solution containing the microorganisms to form a gel entrapping the microorganisms;

(c) soaking the gel entrapping the microorganisms in a solution for a period of time sufficient to reach equilibrium, said solution containing a predetermined concentration of said sugar sufficient to obtain said gel containing said sugar in an amount ranging between at least 100 g/kg and less than 300 g/kg of gel and said solution further containing a predetermined concentration of said polyol sufficient to obtain said gel containing said polyol in an amount of at least 30 g/kg of gel;

(d) separating the equilibrated gel containing the microorganisms from the solution and recovering the gel; and (e) drying the gel to obtain an at least partially dehydrated gel.

21. The gel of claim 20, wherein the solution in which the gel is soaked in step (c) contains a sufficient amount of said sugar to obtain a gel containing said sugar in an amount of at least 200 g/kg of the gel.

22. The gel of claim 20, wherein the gel further contains a protecting substance in a sufficient concentration to improve a viability of the microorganisms during the drying step and to improve a fermentation activity of said microorganisms after a rehydration step.

23. The gel of claim 22, wherein said protecting substance is a non-ionic surfactant.

24. The gel of claim 23, wherein said non-ionic surfactant is a sorbitan ester with a fatty acid.

25. The gel of claim 24, wherein said sorbitan ester is a sorbitan monostearate.

26. The gel defined in claim 20, wherein, during the soaking step, the polyol is present in the solution in an amount of at least 30 g/l to less than 500 g/l.

27. A process for the preparation of an at least partially dehydrated polysaccharide gel entrapping microorganisms and containing a sugar selected from the group consisting of xylose, glucose, fructose, lactose and sucrose, and a polyol selected from the group consisting of sorbitol, inositol and glycerol, wherein said microorganisms exhibit an improved fermentation activity after rehydration as compared with a polysaccharide gel entrapping said microorganisms, which has been at least partially dehydrated in the absence of said sugar, and after rehydration, the process comprising:

(a) dispersing the microorganisms in a gellable polysaccharide solution;

(b) gelling the polysaccharide solution containing the microorganisms to form a gel entrapping the microorganisms;

(c) soaking the gel entrapping the microorganisms in a solution for a period of time sufficient to reach equilibrium, said solution containing a predetermined concentration of said sugar sufficient to obtain said gel containing said sugar in an amount ranging between at least 100 g/kg and less than 300 g/kg of gel and said solution further containing a predetermined concentration of said polyol sufficient to obtain said gel containing said polyol in an amount of at least 30 g/kg of gel;

(d) separating the equilibrated gel containing the microorganisms from the solution and recovering the gel; and (e) drying the gel to obtain an at least partially dehydrated gel.

28. The process of claim 27, wherein the sugar concentration of the solution in which the gel is soaked in step (c) is sufficient to obtain a gel containing said sugar in an amount of at least 200 g/kg of the gel.

29. The process of claim 27, wherein said soaking solution further comprises a protecting substance in a sufficient concentration to improve a viability of the microorganisms during the drying step and to improve a fermentation activity of said microorganisms after the rehydration.

30. The process of claim 29, wherein said protecting substance is a non-ionic surfactant.

31. The process of claim 30, wherein said non-ionic surfactant is a sorbitan ester with a fatty acid.

32. The process of claim 31, wherein said sorbitan ester is a sorbitan monostearate.

33. The process of claim 27, wherein, prior to step (a), a culture of cells of the microorganisms is grown until a stationary growing phase is reached.

34. The process of claim 32, wherein the microorganisms are yeasts, and the yeasts are grown, prior to step (a), until a stationary growing phase is reached, and the yeasts have a degree of initiation of division less than about 5%.

35. The process of claim 27, wherein the gel is prepared in the form of beads or fibers, each of which has a double layer structure comprising an internal layer or core of gel containing the cells of the microorganisms and an external layer or envelope of gel essentially devoid of the microorganisms.

36. The process of claim 27, wherein the gel is prepared in the form of beads, each of which has a diameter of about 2 to 4 mm, and wherein a thickness of an external layer or envelope of the bead is less than 0.8 mm.

37. The process of claim 27, wherein the gel is dried in step (a) until water activity less than 0.5 is obtained.

38. The process of claim 27, wherein the gel is dried in an air stream, and wherein an air temperature and a time of drying is controlled so as to prevent a substantial mortality of the microorganisms.

39. The process of claim 38, wherein the temperature and drying time are selected from the group consisting of 60° C.

during 10 minutes followed by a drying at 35° C. during 110 minutes; 50° C. during 30 to 40 minutes; and 45° C. during 110 minutes.

40. The process of claim 27, wherein said at least partially dehydrated gel is stored in water vapor-tight packaging maintained at a temperature of about 4° C.

41. The process of claim 27, wherein said partially dehydrated gel is stored under vacuum or in a controlled atmosphere, which is low in oxygen content and is enriched in $CO_2$ or nitrogen.

42. The process of claim 27, wherein the gel is dried in step (e) in a fluidized bed.

43. The process of claim 27, wherein the gel is dried in step (e) by lyophilization under vacuum.

44. The process of claim 43, wherein the lyophilization is performed at a lyophilization temperature of −80° C.±10° C.

45. The process defined in claim 27, wherein, during the soaking step, the polyol is present in the solution in an amount of at least 30 g/l to less than 500 g/l.

46. A process for the production of fermented alcoholic drinks by a fermentation step carried out in the presence of immobilized microorganisms comprising preparing the immobilized microorganisms for the fermentation by:
 (a) dispersing the microorganisms in a gellable polysaccharide solution;
 (b) gelling the polysaccharide solution containing the microorganisms to form a gel entrapping the microorganisms;
 (c) soaking the gel entrapping the microorganisms in a solution containing a sugar selected from the group consisting of xylose, glucose, fructose, lactose and sucrose, and a polyol selected from the group consisting of sorbitol, inositol and glycerol for a period of time sufficient to reach equilibrium, said solution containing a predetermined concentration of said sugar sufficient to obtain said gel containing said sugar in an amount ranging between at least 100 g/kg and less than 300 g/kg of gel and said solution further containing a predetermined concentration of said polyol sufficient to obtain said gel containing said polyol in an amount of at least 30 g/kg of the gel;
 (d) separating the equilibrated gel containing the microorganisms from the solution and recovering the gel;
 (e) drying the gel to obtain an at least partially dehydrated gel;
 (f) storing the at least partially dehydrated gel;
 (g) re-hydrating the at least partially dehydrated gel entrapping the microorganisms; and
 (h) using the re-hydrated gel in a fermentation step.

47. The process of claim 46, wherein the sugar concentration of the solution in which the gel is soaked in step (c) is sufficient to obtain a gel containing said sugar in an amount of at least 200 g/kg of the gel.

48. The process of claim 46, wherein said soaking solution further comprises a protecting substance in a sufficient concentration to improve a viability of the microorganisms during the drying step and to improve a fermentation activity of said microorganisms after the re-hydrating step.

49. The process of claim 46, wherein said protecting substance is a non-ionic surfactant.

50. The process of claim 46, wherein said non-ionic surfactant is a sorbitan ester with a fatty acid.

51. The process of claim 46, wherein said sorbitan ester is a sorbitan monostearate.

52. The process of claim 46, wherein, prior to step (a), a culture of cells of the microorganisms is grown until a stationary growing phase is reached.

53. The process of claim 46, wherein the microorganisms are yeasts, and the yeasts are grown, prior to step (a), until a stationary growing phase is reached, and the yeasts have a degree of initiation of division less than about 5%.

54. The process of claim 46, wherein the gel is prepared in the form of beads or fibers, each of which has a double layer structure comprising an internal layer or core of gel containing the cells of the microorganisms and an external layer or envelope of gel essentially devoid of the microorganisms.

55. The process of claim 46, wherein the gel is prepared in the form of beads, each of which has a diameter of about 2 to 4 mm, and wherein a thickness of an external layer or envelope of the bead is less than 0.8 mm.

56. The process of claim 46, wherein the gel is dried in step (a) until water activity less than 0.5 is obtained.

57. The process of claim 46, wherein the gel is dried in an air stream, and wherein an air temperature and a time of drying is controlled so as to prevent the substantial mortality of the microorganisms.

58. The process of claim 57, wherein the temperature and drying time are selected from the group consisting of 60° C. during 10 minutes followed by a drying at 35° C. during 110 minutes; 50° C. during 30 to 40 minutes; and 45° C. during 110 minutes.

59. The process of claim 46, wherein said at least partially dehydrated gel is stored in water vapor-tight packaging maintained at a temperature of about 4° C.

60. The process of claim 46, wherein said partially dehydrated gel is stored under vacuum or in a controlled atmosphere, which is low in oxygen content and is enriched in $CO_2$ or nitrogen.

61. The process of claim 46, wherein the gel is dried in step (e) in a fluidized bed.

62. The process of claim 61, wherein the gel is dried in step (e) by lyophilization under vacuum.

63. The process of claim 62, wherein the lyophilization is performed at a lyophilization temperature of −80° C.±10° C.

64. The process of claim 46, wherein said dehydrated gel is submitted to a reactivation step before it is used in the fermentation step.

65. The process of claim 46, wherein said polyol is glycerol.

66. The process of claim 46, wherein the fermented alcoholic drink is wine and the microorganisms are selected from bacteria and yeasts.

67. The process of claim 66, wherein said yeast is *Saccharomyces cerevisiae,* and said bacteria is a lactic bacteria.

68. In a process for the second fermentation of wine in the presence of immobilized yeasts, and in closed vessels, the improvement which comprises preparing the immobilized yeasts for the second fermentation by:
 (a) dispensing the yeasts in a gellable polysaccharide solution;
 (b) gelling the polysaccharide solution containing the yeast to form a gel entrapping the yeasts;

(c) soaking the gel entrapping the yeasts in a solution containing a sugar selected from the group consisting of xylose, glucose, fructose, lactose and sucrose, and a polyol selected from the group consisting of sorbitol, inositol and glycerol for a period of time sufficient to reach equilibrium, said solution containing a predetermined concentration of said sugar sufficient to obtain said gel containing said sugar in an amount ranging between at least 100 g/kg and less than 300 g/kg of gel and said solution further containing a predetermined concentration of said polyol sufficient to obtain said gel containing said polyol in an amount of at least 30 g/kg of the gel;

(d) separating the equilibrated gel containing the yeasts from the solution and recovering the gel; and (e) drying the gel to obtain an at least partially dehydrated gel;

(f) storing the at least partially dehydrated gel;

(g) re-hydrating the at least partially dehydrated gel entrapping said yeasts; and (h) using the re-hydrated gel in a second fermentation of wine.

69. The process of claim 68, wherein a sparkling wine is obtained.

70. The process of claim 68, wherein the sugar concentration of the solution in which the gel is soaked in step (c) is sufficient to obtain a gel containing said sugar in an amount of at least 200 g/kg of the gel.

71. The process of claim 68, wherein said gel further comprises a protecting substance in a sufficient concentration to improve a viability of the yeasts during the drying step and to improve a fermentation activity of the yeasts after the re-hydrating step.

72. The process of claim 68, wherein said protecting substance is a non-ionic surfactant.

73. The process of claim 72, wherein said non-ionic surfactant is a sorbitan ester with a fatty acid.

74. The process of claim 73, wherein said sorbitan ester is a sorbitan monostearate.

75. The process of claim 68, wherein, prior to step (a), a culture of cells of the yeasts is grown until a stationary growing phase is reached.

76. The process of claim 68, wherein the yeasts are grown, prior to step (a), until a stationary growing phase is reached, and the yeasts have a degree of initiation of division less than about 5%.

77. The process of claim 68, wherein the gel is prepared in the form of beads or fibers, each of which has a double layer structure comprising an internal layer or core of gel containing the cells of the yeasts and an external layer or envelope of gel essentially devoid of the yeasts.

78. The process of claim 68, wherein the gel is prepared in the form of beads, each of which has a diameter of about 2 to 4 mm, and wherein a thickness of an external layer or envelope of the bead is less than 0.8 mm.

79. The process of claim 68, wherein the gel is dried in step (a) until water activity less than 0.5 is obtained.

80. The process of claim 68, wherein the gel is dried in step (e) in an air stream, the air temperature and the time of drying being controlled to prevent the substantial mortality of the yeasts.

81. The process of claim 68, wherein the temperature and drying time are selected from the group consisting of 60° C. during 10 minutes followed by a drying at 35° C. during 110 minutes; 50° C. during 30 to 40 minutes; and 48° C. during 110 minutes.

82. The process of claim 68, wherein said at least partially dehydrated gel is stored under vacuum or in a water vapor-tight packaging maintained at a temperature of about 4° C.

83. The process of claim 68, wherein said partially dehydrated gel is stored under vacuum or in a controlled atmosphere, which is low in oxygen content and is enriched in $CO_2$ or nitrogen.

84. The process of claim 68, wherein the gel is dried in step (e) in a fluidized bed.

85. The process of claim 68, wherein the gel is dried in step (e) by lyophilization under vacuum.

86. The process of claim 68, wherein the lyophilization is performed at a lyophilization temperature of −80° C.±10° C.

87. The process of claim 68, wherein said dehydrated gel is reactivated before it is used to said second fermentation.

88. The process defined in claim 68, wherein, during the soaking step, the polyol is present in the solution in an amount of at least 30 g/l to less than 500 g/l.

* * * * *